United States Patent
Schulhof et al.

(10) Patent No.: US 9,022,995 B2
(45) Date of Patent: May 5, 2015

(54) STOPPER/PLUNGER FOR CARPULES OF SYRINGE-CARPULE ASSEMBLY

(75) Inventors: Steven Schulhof, Teaneck, NJ (US); Bruce Freund, Demarest, NJ (US); Mark Foyil, Hillsborough, NJ (US)

(73) Assignee: Synchrojet LLC, Teaneck, NJ (US)

( * ) Notice: Subject to any disclaimer, the term of this patent is extended or adjusted under 35 U.S.C. 154(b) by 925 days.

(21) Appl. No.: 13/195,658

(22) Filed: Aug. 1, 2011

(65) Prior Publication Data

US 2013/0035666 A1 Feb. 7, 2013

(51) Int. Cl.
| | | |
|---|---|---|
| *A61M 5/315* | (2006.01) | |
| *A61M 5/24* | (2006.01) | |
| *A61J 1/06* | (2006.01) | |
| *A61M 5/31* | (2006.01) | |

(52) U.S. Cl.
CPC .............. *A61M 5/2448* (2013.01); *A61J 1/062* (2013.01); *A61M 5/31511* (2013.01); *A61M 5/31596* (2013.01); *A61M 2005/2414* (2013.01); *A61M 2005/3123* (2013.01)

(58) Field of Classification Search
CPC .......... A61J 1/062; A61M 2005/3123; A61M 5/31511
USPC ........................... 604/218, 220, 221, 232, 415
See application file for complete search history.

(56) References Cited

U.S. PATENT DOCUMENTS

| | | | |
|---|---|---|---|
| 4,031,892 A | 6/1977 | Hurschman | |
| 4,306,357 A | 12/1981 | Villarejos | |
| 4,413,991 A | 11/1983 | Schmitz et al. | |
| 4,755,169 A | 7/1988 | Sarnoff et al. | |
| 4,873,193 A | 10/1989 | Jensen et al. | |
| 5,037,402 A | 8/1991 | Bartman | |
| 5,171,220 A | 12/1992 | Morimoto | |
| 5,232,109 A | 8/1993 | Tirrell et al. | |
| 5,286,257 A | 2/1994 | Fischer | |
| 5,330,426 A | 7/1994 | Kriesel et al. | |
| 5,364,369 A | 11/1994 | Reynolds | |

(Continued)

FOREIGN PATENT DOCUMENTS

| | | |
|---|---|---|
| DE | 102006040888 B3 | 11/2007 |
| EP | 0302248 A1 | 2/1989 |

(Continued)

OTHER PUBLICATIONS

Written Opinion of the International Searching Authority, May 31, 2011 in PCT/US2010/052609.

(Continued)

*Primary Examiner* — Nicholas Lucchesi
*Assistant Examiner* — Deanna K Hall
(74) *Attorney, Agent, or Firm* — Ostrager Chong Flaherty & Broitman P.C.

(57) ABSTRACT

An elastomeric stopper that can be partially inserted in a rear opening of a glass carpule and that also serves, when fully inserted in the carpule, as a plunger for forcing fluid inside the carpule out through a front opening thereof. The stopper has a thin central portion at its front end that can be readily pierced by a pointed hollow rod of a syringe. When the hollow rod is removed, the elastomeric material of the thin central portion will "seal itself" around the puncture hole. The stopper also has a retractable lip at its rear end that allows the entirety of the stopper to be pushed down and into a fluid-containing glass carpule, thereby acting as a plunger and ejecting fluid from the front opening of the carpule.

6 Claims, 8 Drawing Sheets

(56) References Cited

U.S. PATENT DOCUMENTS

| | | | |
|---|---|---|---|
| 5,429,610 | A | 7/1995 | Vaillancourt |
| 5,476,449 | A | 12/1995 | Richmond |
| 5,496,284 | A | 3/1996 | Waldenburg |
| 5,580,786 | A | 12/1996 | Gombrich et al. |
| 5,665,068 | A | 9/1997 | Takamura |
| 5,685,846 | A | 11/1997 | Michaels, Jr. |
| 5,713,857 | A | 2/1998 | Grimard et al. |
| 5,788,670 | A | 8/1998 | Reinhard et al. |
| 5,971,953 | A | 10/1999 | Bachynsky |
| 6,132,400 | A | 10/2000 | Waldenburg |
| 6,468,250 | B2 | 10/2002 | Yang |
| 6,692,468 | B1 | 2/2004 | Waldenburg |
| 6,972,005 | B2 | 12/2005 | Boehm, Jr. et al. |
| 2005/0245880 | A1 | 11/2005 | Howlett et al. |
| 2006/0178644 | A1 | 8/2006 | Reynolds |
| 2010/0016807 | A1 | 1/2010 | Thilly |
| 2010/0106139 | A1 | 4/2010 | Schulhof |

FOREIGN PATENT DOCUMENTS

| | | |
|---|---|---|
| EP | 0815885 A1 | 1/1998 |
| WO | 2012019983 A1 | 2/2012 |

OTHER PUBLICATIONS

International Search Report and Written Opinion dated Feb. 26, 2013, from International Application No. PCT/US2012/049142, foreign counterpart to the instant application.

Extended European Search Report in corresponding European Application No. 12820656.2, mailed from European Patent Office Mar. 4, 2015.

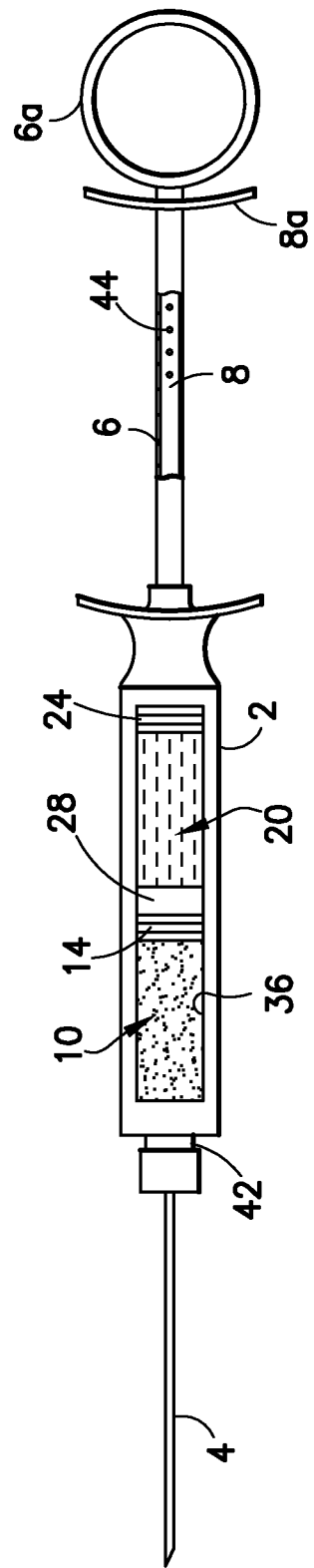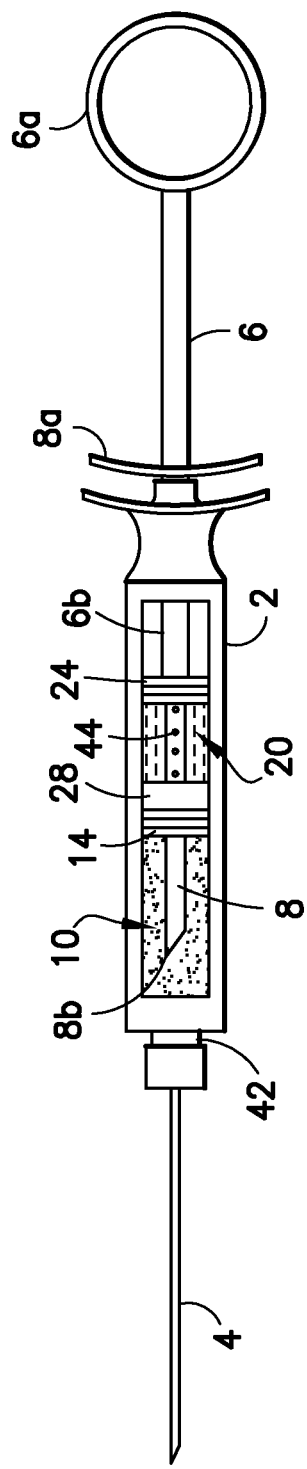

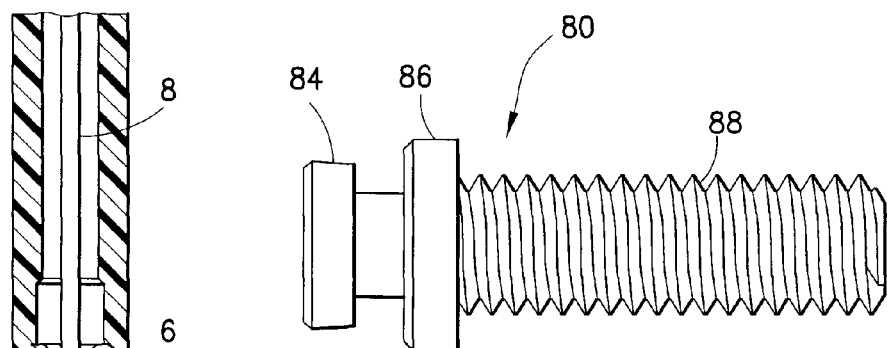
FIG. 17
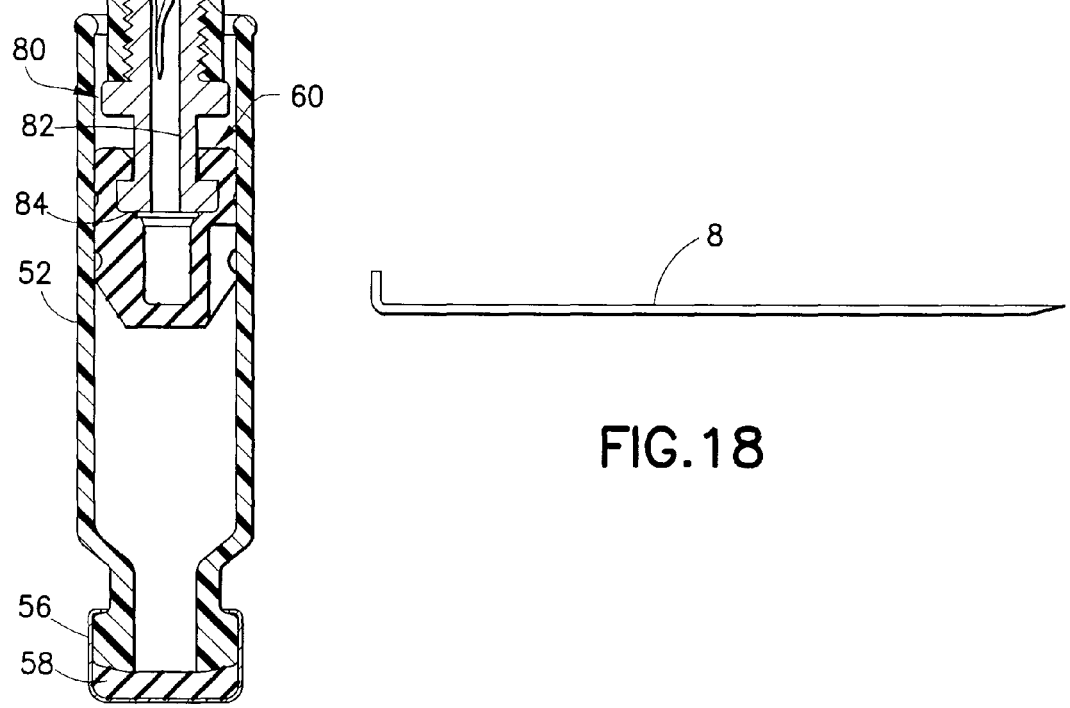
FIG. 16
FIG. 18

STOPPER/PLUNGER FOR CARPULES OF SYRINGE-CARPULE ASSEMBLY

BACKGROUND

Conventionally powdered medicine, liquid solvents and an injection device are normally used when powdered injection medicines are given. The powdered medicines are filled aseptically into a vial or an ampule container (referred to as a "carpule" hereinafter). As liquid solvents, distilled water for injection or an isotonic sodium chloride solution are filled aseptically in an ampule or carpule. Typically a syringe is used as the injection device.

It is known in the prior art to provide a syringe having two chambers for use in delivering drugs to medical patients. In particular, dual-chamber syringes are known that allow solid medicine (such as lyophilized material or powder) and liquid solvent (such as water or saline) to be pre-mixed prior to injection into a patient.

U.S. patent application Ser. No. 12/607,498 discloses an improved system to enable the delivery of drugs that come in two forms (i.e. lyophilized matter or powder and liquid solvent) that need to be premixed in an easy, single use, such as when injecting botulinum toxin. The improved system is sterilizable, uses disposable carpules, and allows blood to be aspirated to alert the operator that he/she is mistakenly in a blood vessel. The improved system is a syringe-carpule assembly comprising two carpules, a housing holding the carpules in an end-to-end relationship, an outer hollow plunger rod supported by and slidable relative to the housing, and an inner perforated hollow rod slidably arranged inside the outer hollow plunger rod. The inner perforated hollow rod, when fully extended, has perforations in both carpules, allowing the interior chambers of the carpules to be in fluid communication. Liquid solvent in the rear carpule is then injected into the front carpule, which comprises an evacuated chamber containing solid matter that dissolves in the presence of that solvent to form a mixture. The rear carpule is then removed from the syringe and the mixture in the front carpule is injected into the patient using a needle attached to the end of the syringe housing.

The above-described carpule-syringe assembly is especially useful when the front carpule initially contains only freeze-dried matter, such as lyophilized botulinum toxin. Freeze-drying (also known as lyophilization or cryodesiccation) is a dehydration process typically used to preserve a perishable material or make the material more convenient for transport. The freeze-drying process involves freezing the material and then dehydrating the material by reducing the surrounding pressure to allow the frozen water in the material to sublime directly from the solid phase to the gas phase.

Pharmaceutical manufacturers use lyophilization processes in order to extend the shelf life of certain drugs. In the lyophilization process, a liquid drug contained in a carpule is subjected to a freeze-drying process to extract the aqueous content from the drug, leaving the active components of the drug in a crystalline state in the evacuated and then sealed carpule.

It is known to provide a so-called "lyophilization stopper" comprising a plug with a flange at one end, which plug also has a passage or groove which facilitates extraction of the vaporized aqueous content when the plug is only partially inserted. The lyophilization stopper includes recesses which, when the stopper is partially inserted into a rear opening of an otherwise sealed carpule containing material to be freeze-dried, facilitates fluid communication between the interior of the carpule and the freeze dryer, allowing vapors generated during the lyophilization process to escape from the carpule. After the lyophilization operation, shelves provided within the freeze dryer are typically lowered to contact the stopper and then push it deeper into the carpule to a position whereat the evacuated chamber of the carpule, with its dehydrated contents, is sealed for later use.

There is a need for an improved system to enable the delivery of drugs that come in two forms (i.e. lyophilized matter or powder and liquid solvent) that need to be premixed in an easy, single use, such as when injecting botulinum toxin. Preferably the improved system is sterilizable, uses disposable carpules, and allows blood to be aspirated to alert the operator that he/she is mistakenly in a blood vessel.

SUMMARY

An improved system for satisfying the foregoing needs comprises an elastomeric lyophilization stopper that can be partially inserted in a rear opening of a glass carpule and is movable from a freeze-drying position to a sealed position, and that also serves as a plunger for forcing fluid inside the carpule out through a front opening thereof during injection of fluid into another carpule or into a patient.

In accordance with the embodiments disclosed herein, the elastomeric lyophilization stopper can be partially inserted in a rear opening of a glass carpule and also serves, when fully inserted in the carpule, as a plunger for forcing fluid inside the carpule out through a front opening thereof. The lyophilization stopper has a thin central portion at its front end that can be readily pierced by a pointed hollow rod of a syringe. When the hollow rod is removed, the elastomeric material of the thin central portion will "seal itself" around the puncture hole. The lyophilization stopper (hereinafter "lyostopper") also has a retractable lip at its rear end that allows the entirety of the stopper to be pushed down and into a fluid-containing glass carpule, thereby acting as a plunger and ejecting fluid from the front opening of the carpule.

In the particular application disclosed herein, i.e., a dual-chamber syringe in which one carpule contains freeze-dried material and the other carpule contains diluent, each carpule of the syringe/carpule assembly has a lyostopper partially inserted in its rear opening. In the case of the diluent-containing carpule, the lyostopper is partially inserted until it reaches a sealed position (i.e., the diluent-containing chamber of the carpule is sealed). In the case of the carpule that contains freeze-dried material, the lyostopper will again be partially inserted to seal the freeze-dried material in the carpule chamber after freeze-drying. However, during the freeze-drying process which precedes the sealing operation, the lyostopper is partially inserted less deeply into the carpule and does not reach the sealed position. In this freeze-drying position, one or more recesses formed in the lyostopper allow the freeze dryer to be in fluid communication with the interior chamber of the carpule. This fluid communication allows vapors to escape from the carpule chamber during the freeze drying process.

The structure of the lyostopper disclosed herein facilitates usage of the syringe-carpule assembly to perform both pre-mixing and injection. The syringe holds front and rear carpules during pre-mixing and then retains only the front carpule for injection. The rear carpule contains diluent and the front carpule contains lyophilized matter. A needle is attached to the front end of the syringe, piercing the front seal of the front carpule. During pre-mixing, an inner hollow perforated rod of the syringe pierces the lyostoppers in the front and rear carpules and then an outer hollow plunger rod is manually operated to push the lyostopper in the rear carpule forward until the diluent (e.g., saline) is pushed through the inner hollow perforated rod and into the front carpule. The needle allows air to vent out of the front carpule during this pre-mixing operation. Then the inner and outer hollow rods are retracted and the rear carpule is removed. At this juncture the previously punctured lyostoppers reform a seal. The distal end of the outer hollow plunger rod is then coupled to the lyostopper in the front carpule and manually operated to push that lyostopper forward to inject the pre-mixed solution into the patient via the needle.

As should be understood from the foregoing, the unique structure of the lyostopper disclosed herein enables it to be used as both a seal and a plunger during the administration of medicine, that dual function being in addition to the lyostopper's venting function when included as part of a freeze-drying process.

One aspect of the invention is an assembly comprising a carpule comprising a bead surrounding an opening at one end thereof and a stopper at least partly inserted in the carpule at the one end, the stopper being a body of elastomeric material comprising a venting portion, a sealing portion and a retracting portion, the venting portion comprising at least one venting channel and at least one outer circumferential groove for receiving a portion of the carpule bead when the elastomeric body is partly inserted in the carpule in a venting position, the sealing portion comprising an annular outer circumferential groove for receiving the carpule bead when the elastomeric body is inserted further but not fully in the carpule in a sealing position, and the retracting portion comprising a lip that is disposed outside the carpule when the elastomeric body is partly inserted in the carpule and that flexes radially inward when the elastomeric body is fully inserted in the carpule, the sealing portion being disposed between the venting portion and the retracting portion.

Another aspect of the invention is an assembly comprising: a syringe comprising a housing and a movable element comprising a head; a carpule disposed inside the housing, the carpule comprising a bead surrounding an opening at one end thereof; and a stopper at least partly inserted in the carpule opening, the stopper being a body of elastomeric material comprising a sealing portion, a retracting portion and a cavity occupied by the head of the syringe, the sealing portion comprising an annular outer circumferential groove for receiving the carpule bead when the elastomeric body is partly inserted in the carpule, and the retracting portion comprising a lip that is disposed outside the carpule when the elastomeric body is partly inserted in the carpule and that flexes radially inward when the elastomeric body is fully inserted in the carpule.

A further aspect of the invention is a body made of elastomeric material and suitable for use as a lyostopper/plunger, the elastomeric body comprising: a pierceable closed front end; a rear end having a circular central opening and comprising an annular lip that is concentric with and surrounds the circular central opening; an internal cavity that starts at the opening and ends behind and adjacent to the closed front end; a plurality of channels formed at equiangular intervals; a plurality of outer circumferential grooves disposed along a common circle and extending between respective pairs of the channels; and an annular outer circumferential groove disposed along a circle lying in a plane that is generally parallel to a plane of the common circle, the annular outer circumferential groove being disposed between the annular lip and the plurality of outer circumferential grooves.

Yet another aspect of the invention is a method of using a syringe, comprising: (a) placing first and second carpules in a housing of a syringe in an end-to-end relationship with the first carpule in front of the second carpule, each of the first and second carpules having a sealed front opening and a rear opening closed by a respective stopper, the first carpule containing solid matter and the second carpule containing liquid diluent; (b) piercing the sealed front opening of the first carpule with a needle; (c) inserting a head on a hollow plunger rod of the syringe into a cavity formed in the stopper of the second carpule; (d) extending a pointed hollow rod of the syringe to cause its tip to pierce the stopper of the second carpule, the sealed front opening of the second carpule and the stopper of the first carpule in sequence; and (e) while the tip of the pointed hollow rod is inside the first carpule and the head on the hollow plunger rod is inside the cavity in the stopper of the second carpule, extending the hollow plunger rod so that the head pushes the stopper of the second carpule further into the second carpule, causing fluid in the second carpule to be transferred to the first carpule via the pointed hollow rod.

Other aspects of the invention are disclosed and claimed below.

BRIEF DESCRIPTION OF THE DRAWINGS

FIG. 1 is a drawing showing two carpules respectively containing botulinum toxin and saline.

FIG. 2 is a drawing showing a rectangular piece of adhesive tape that is wrapped around respective portions of the carpules depicted in FIG. 1 to couple those carpules together in end-to-end relationship.

FIG. 4 is a drawing showing portions of a syringe-carpule assembly that includes the coupled carpules depicted in FIG. 2. The device is shown in a state wherein botulinum toxin in the forward carpule and saline solution in the rearward carpule have not yet been mixed.

FIG. 5 is a drawing showing the same assembly depicted in FIG. 4, with the difference that an inner perforated hollow rod has been advanced to a position whereat the saline solution in the rearward carpule can be injected into the forward carpule.

FIG. 16 is a drawing showing the same configuration as seen in FIG. 14 (i.e., the inner hollow perforated rod of the syringe is in a retracted position), except that the lyostopper/plunger has been fully inserted inside the carpule by extension of the outer hollow plunger rod.

FIG. 17 is a drawing showing a side view of the flat head plunger rod screw seen in FIGS. 14-16.

FIG. 18 is a drawing showing a side view of the needle seen in FIGS. 14-16.

Reference will hereinafter be made to the drawings in which similar elements in different drawings bear the same reference numerals.

DETAILED DESCRIPTION

Figures 1, 2:
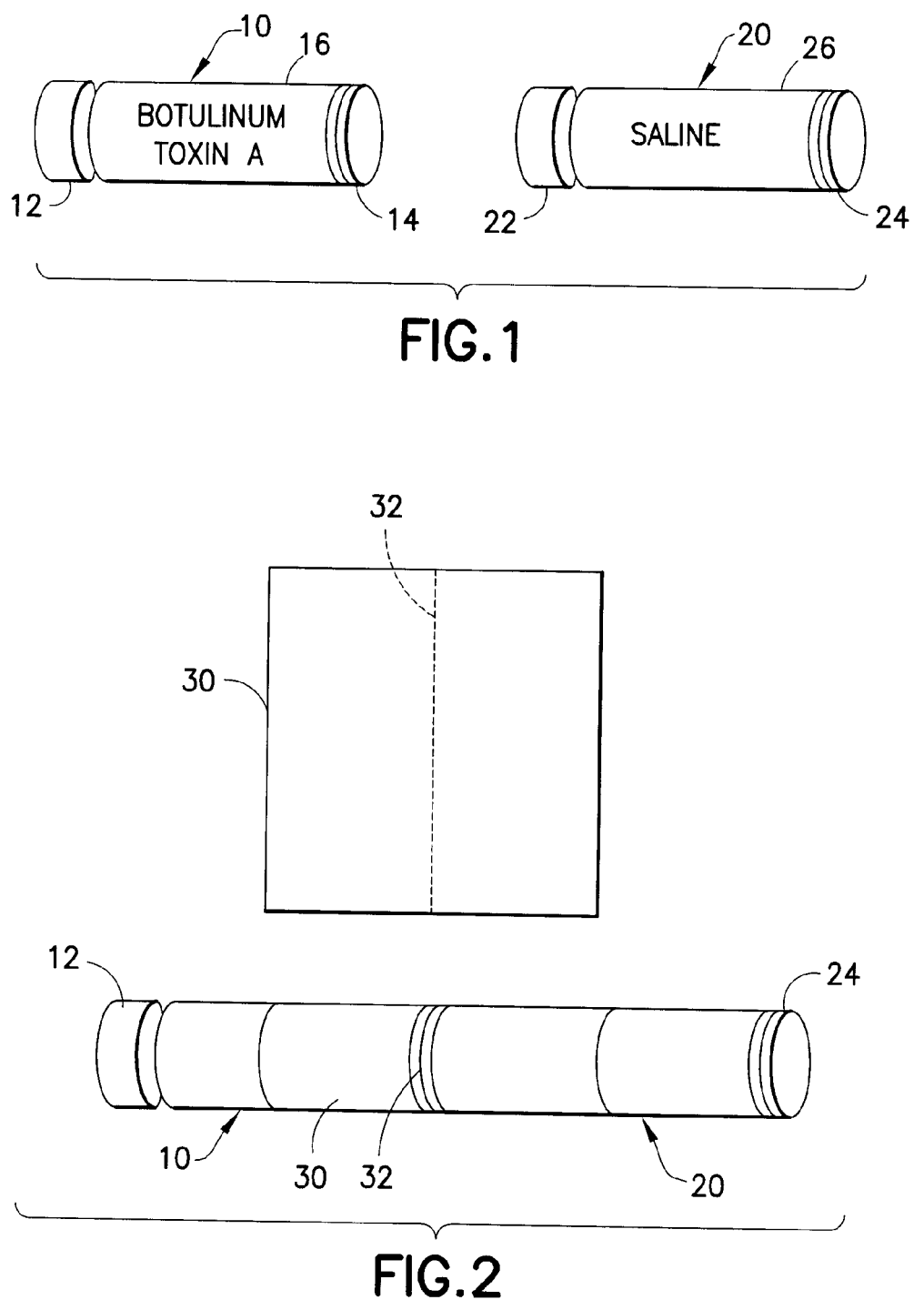
Figure 3:
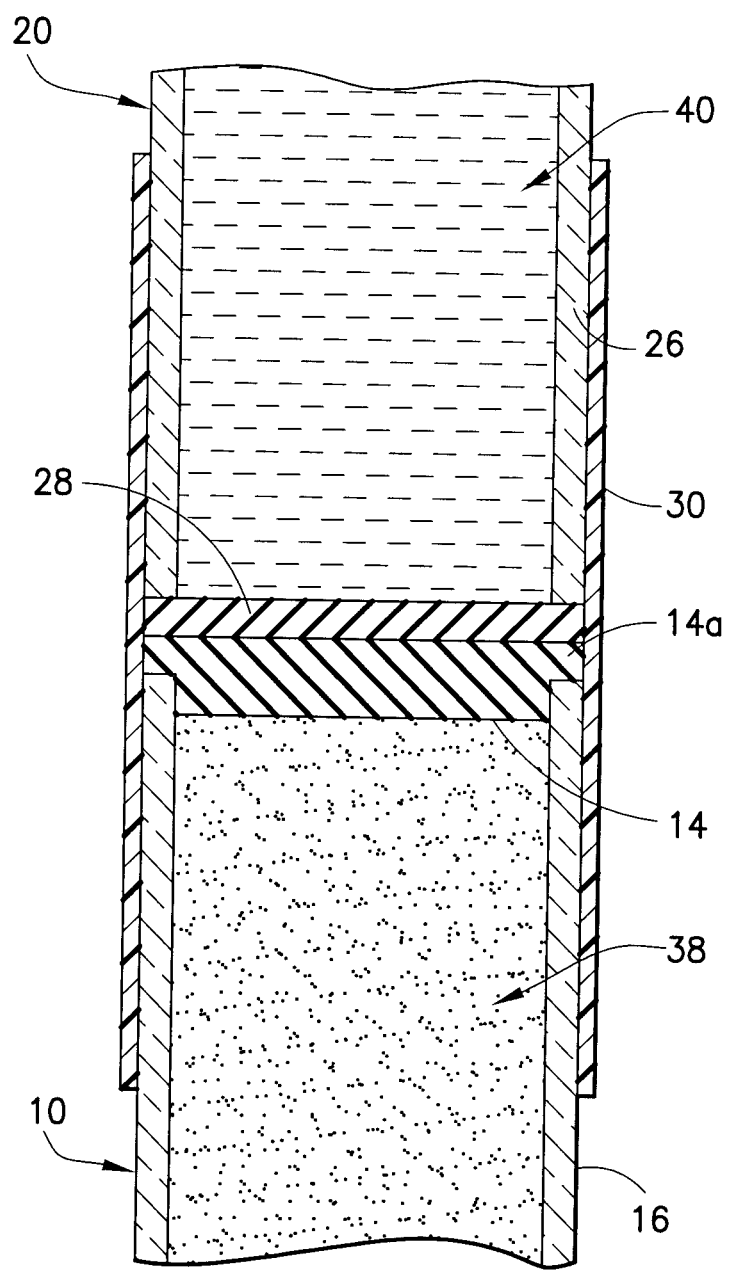
FIG. 3 is a sectional view showing respective portions of the coupled carpules depicted in FIG. 2.

A method and an apparatus for administering a medicine to a medical patient in accordance with one embodiment will now be described with reference to FIGS. 1-7. Two carpules are arranged end-to-end and then inserted into a syringe. The first carpule has an evacuated chamber containing lyophilized matter or powder; the second carpule contains liquid solvent.

In the example disclosed hereinafter, the first carpule 10 (see FIG. 1) contains botulinum toxin while the second carpule 20 contains saline. Carpule 10 comprises a generally cylindrical glass vial 16 with openings at both ends. The forward end of vial 16 is covered by a rubber membrane (not shown in FIG. 1) that is held in place by a cap 12 made of metal foil. Although not shown in FIG. 1, it is known that the cap 12 has a circular opening (not shown) at its center that exposes a portion of the aforementioned rubber membrane. The rearward end of vial 10 is closed by a rubber stopper 14. Carpule 20 comprises a generally cylindrical glass vial 26 with openings at both ends. The forward end of vial 26 is covered by a rubber membrane (not shown in FIG. 1) that is held in place by a cap 22 made of metal foil. Cap 22 also has a circular opening (not shown) at its center that exposes a portion of the rubber membrane. The rearward end of vial 26 is closed by a rubber stopper 24.

The carpules 10 and 20 depicted in FIG. 1 can be arranged so that their centerlines are collinear, with the cap 22 of carpule 20 abutting the rubber stopper 14 of carpule 10. To hold the carpules in this end-to-end relationship, a rectangular piece of adhesive tape 30 (or other flexible substrate) is wrapped around respective portions of carpules 10 and 20, as seen in FIG. 2. The tape piece 30 has a line 32 of weakened tear resistance (e.g., a row of small perforations spaced at regular intervals). The tape piece should be positioned such that when it is wrapped around the abutting carpules, the tear line 32 is disposed in a plane perpendicular to the axes of the carpules and is aligned with the interface between the abutting carpules. As will be explained later, the tear line 32 facilitates the separation of the coupled carpules at a later stage in the method for administering medicine disclosed herein.

FIG. 3 is a sectional view showing respective portions of the coupled carpules except that, for ease of illustration, the metal cap 22 of carpule 20 has been omitted. That metal cap, if shown in FIG. 3, would have a circumferential portion disposed between the vial 26 and the adhesive tape 30 and an annular portion disposed between the rubber stopper 14 of carpule 10 and the rubber membrane 28 of carpule 20. The rubber stopper 14 includes a portion disposed within the vial 16 and a flange portion 14a that is trapped between the rear end surface of vial 16 and the front end of carpule 20. This arrangement serves to hold the rubber stopper 14 in position when it is penetrated by an inner perforated hollow rod of the syringe, as will described hereinafter with reference to FIGS. 5 and 7.

As seen in FIG. 3, carpule 10 contains lyophilized botulinum toxin 38 and carpule 20 contains saline solution 40. As is well known in the art, the lyophilized botulinum toxin must be dissolved in the saline solution before it can be injected into a patient. This is accomplished using the syringe depicted in FIG. 4.

FIG. 4 shows portions of a syringe-carpule assembly in accordance with one embodiment of the invention, which assembly includes the coupled carpules depicted in FIG. 2. The device is shown in a state wherein the lyophilized botulinum toxin in the forward carpule 10 and the saline solution in the rearward carpule 20 have not yet been mixed and a needle 4 has been screwed onto the syringe housing.

The syringe comprises a housing 2 capable of holding the coupled carpules 10 and 20 such that carpule 10 is in front of carpule 20, an outer hollow plunger rod 6 supported by and slidable relative to the housing 2, and an inner hollow rod 8 arranged inside the outer hollow plunger rod 6. The inner hollow rod 8 and the outer hollow plunger rod each comprise respective circular cylindrical tube portions, one slidable within the other. More specifically, the outer diameter of inner hollow rod 8 is slightly less than the inner diameter of outer hollow plunger rod 8, with sufficient clearance to allow the former to easily slide within the latter.

The housing 2 has a window 36 through which the coupled carpules can be inserted. A device, such as a swinging metal door (or other member) with a latch for locking it in a closed position, could be provided in the area of the front carpule 10 to hold it in place while the rear carpule 20 is being removed, as will be discussed later. The housing also has a threaded boss 42 to which needle 4 is attached. The threaded boss 42 has a bore through which the rear end of the needle can penetrate the rubber membrane on the forward end of the front carpule 10 during needle attachment. After the needle has been attached, the syringe-carpule-needle assembly is held in a vertical position with the needle pointing upward during the pre-mixing operation.

The inner hollow rod 8 is a circular cylindrical tube that is angled at its forward tip 8b. The space inside the hollow rod 8 forms a channel that ends as an opening in the angled forward tip 8b. The wall of the inner hollow rod is provided with a plurality of perforations or openings 44 arranged in two diametrically opposed rows (only one of these two rows is visible in FIGS. 4-6). The perforations 44 communicate with the open tip of inner hollow rod 8 via the channel therein. The inner hollow rod 8 is slidable between an extended position and a retracted position by the operator manipulating a handle 8a of the inner hollow rod 8. The handle 8a is slidable along the outside of the outer hollow plunger rod 6. The wall of the outer hollow plunger rod 6 has a longitudinal slot (not shown) that allows the handle 8a to be connected to the circular cylindrical wall of the inner hollow rod 8. This allows the inner hollow rod 8 to be slided by operation of handle 8a.

The inner hollow rod 8 is shown retracted in FIG. 4 and extended in FIG. 5. As seen in FIG. 4, in its retracted position the inner hollow rod 8 does not project into either carpule 10 or 20. As seen in FIG. 5, in its extended position inner hollow rod 8 projects through carpule 20 and the angled tip 8b of the inner hollow rod 8 projects into carpule 10. The angled or pointed tip 8b penetrates the rubber stopper 24 and rubber membrane 28 of carpule 20 and also penetrates the rubber stopper 14 of carpule 10. In the fully extended position of inner hollow rod 8, the opening at the angled tip 8b is disposed within carpule 10 and at least one and preferably more than one perforation 44 is disposed within carpule 20. Since inner rod 8 is hollow, in its fully extended position the inner hollow rod 8 provides a channel for flow communication between the internal chambers of carpules 10 and 20. Since the pressure inside the evacuated internal chamber of carpule 10 is lower than the pressure inside the liquid-filled carpule 20, the saline solution inside carpule 20 is initially drawn into carpule 10 by the pressure differential, flowing through the inner hollow rod 8. The outer hollow plunger rod 6 is then pushed forward until the head 6b thereof engages the rubber stopper 24. Then the outer hollow plunger rod 6 is pushed further forward, which causes the rubber stopper 24 to also move forward, thereby forcing liquid out of carpule 20 and into carpule 10 via the inner hollow rod 8. The needle 4, which has punctured the forward membrane of the front carpule 10, allows air to vent out of the front carpule 10 as it fills with liquid from carpule 20.

Figure 6:
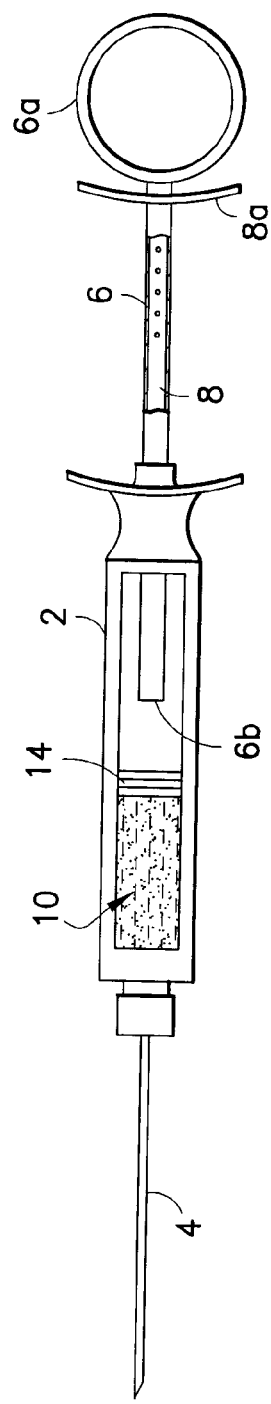
FIG. 6 is a drawing showing the same assembly depicted in FIGS. 4 and 5 after the botulinum toxin and saline solution have been mixed in the forward carpule and the rearward carpule has been removed.

After the saline solution has been injected into the carpule 10, the inner hollow rod 8 is retracted, again by operator manipulation of the handle 8a. The substantially empty rear carpule 20 is then removed by tearing the adhesive tape 30 along its tear line 32. The saline solution now inside carpule 10 dissolves the lyophilized botulinum toxin. FIG. 6 shows the syringe with attached needle 4 and with the second carpule removed.

The outer hollow plunger rod 6 is slidable between retracted and extended positions relative to the syringe housing 2. The front end of outer hollow plunger rod 6 carries a head 6b (seen in FIGS. 5-7) having an opening that allows passage therethrough of the pointed tip 8b of inner hollow rod 8. The head 6b is disposed within carpule 10 (not shown in the drawings) when the outer hollow plunger rod 6 is in its fully extended position, and is not disposed within carpule 10 when the outer hollow plunger rod 6 is in its fully retracted position. The head 6b is preferably an annular ring that screws onto the end of the outer hollow plunger rod 6. The opening of that annular ring 6b allows the inner hollow rod 8 to pass through. The ring 6b can be unscrewed and removed to allow access to the inner hollow rod 8.

Figure 7:
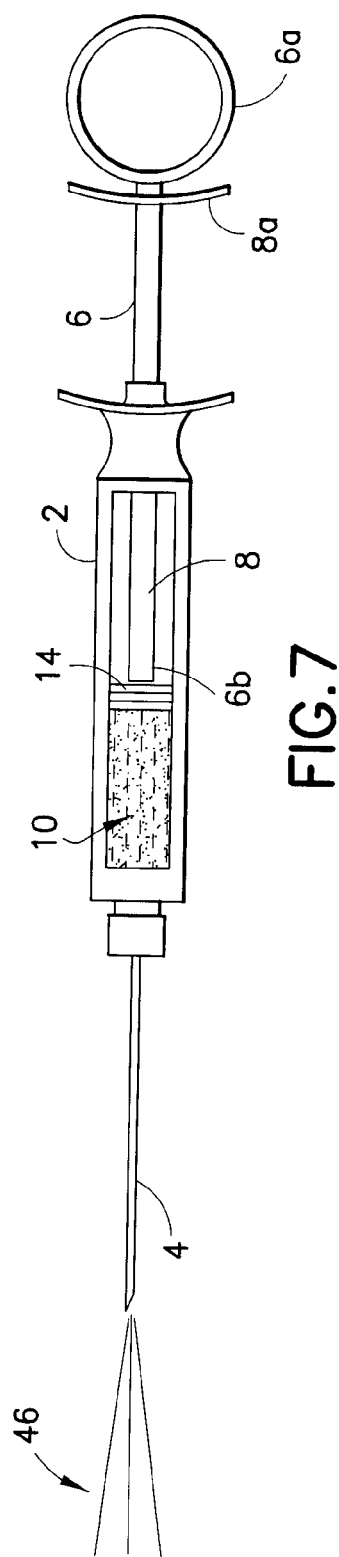
FIG. 7 is a drawing showing the same assembly depicted in FIG. 6 as the mixture in the forward carpule is being injected into a medical patient (not shown).

After the doctor inserts the needle 4 into the patient, the doctor injects the medicine into the patient. This is accomplished by the operator moving the outer hollow plunger rod 6 from its retracted position until head 6b engages the rubber stopper 14 residing in the rear opening of the front carpule 10 (see FIG. 7). As the outer hollow plunger rod 6 is moved forward of its position depicted in FIG. 7, i.e., toward its fully extended position, by the operator, the flat annular head 6b of the advancing outer plunger rod 6 pushes the rubber stopper 14 toward the front end of carpule 10. As the rubber stopper 14 moves forward, it forces the mixture 40 of dissolved botulinum toxin and saline solution through and out the needle 4, as seen in FIG. 7.

In accordance with an alternative embodiment, the head of the outer hollow plunger rod 6 can take the form of a harpoon or triangle. Such a head would be shaped and dimensioned such that as the head bears against the slits formed in rubber stopper 14, the detents or wings projecting on opposite sides of the triangular head (beyond the radius of the outer plunger rod) would engage the rubber stopper 14. The frictional forces would be such that the rubber stopper 14 would be effectively coupled to the triangular head, whether the outer hollow plunger rod 6 were being extended or retracted. This has the advantage that blood from the patient could be aspirated by pulling the rubber stopper 14 back a short distance.

A method and an apparatus for administering a medicine to a medical patient in accordance with a further embodiment will now be described with reference to FIGS. 8-18. Again two carpules are arranged end-to-end and then inserted into a syringe. The first carpule has an evacuated chamber containing lyophilized matter or powder; the second carpule contains liquid solvent.

Figure 8:
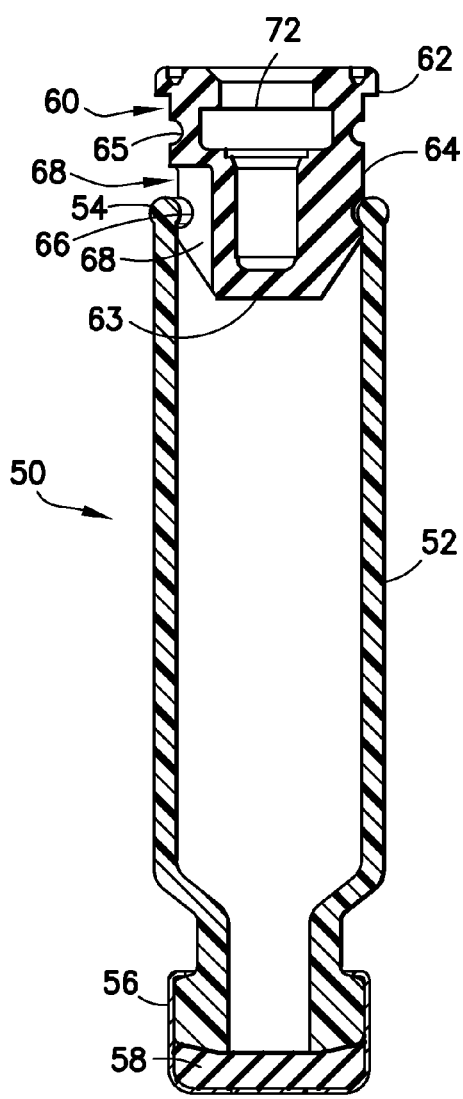
FIG. 8 is a drawing showing a cross-sectional view of a carpule having a portion of a lyostopper/plunger partially inserted in a rear opening of the carpule, which partially inserted position is adopted during lyophilization.

FIG. 8 shows a cross-sectional view of an assembly 50 comprising a glass carpule 52 having respective openings at its necked front end and its rear end. The forward end (i.e., head) of necked carpule 52 is covered by a rubber membrane 58 that is held in place by a cap 56 made of metal foil. Cap 56 has a circular opening (not shown) at its center that exposes a portion of rubber membrane 58. The opening at the rear end is surrounded by a bead 54.

During lyophilization of solid matter contained in carpule 52, the stopper/plunger 60 occupies the venting (partially inserted) position shown in FIG. 8. The same stopper/plunger is also partially inserted in carpules containing only liquid diluent, but because such carpules are not placed in a freeze dryer, there is no need for the stopper/plunger in diluent-containing carpules to adopt the position shown in FIG. 8. As will be described later (with reference to FIG. 13), the stopper/plunger in a diluent-containing carpule will be partially inserted further into the carpule than is shown in FIG. 8, this further partially inserted position being the position at which the stopper/plunger seals the rear opening of the carpule (i.e., its sealed position).

The details of the structure of stopper/plunger 60 are best described with reference to FIGS. 9-12, which show different views of the stopper/plunger in isolation. Stopper/plunger 60 is a body made of elastomeric material. This elastomeric body comprises: a pierceable closed front end 63 (see FIG. 10); a rear end having a chamfered circular central opening 70 and comprising an annular lip 62 that is concentric with and surrounds the chamfered circular central opening 70 (see FIG. 10); an internal cavity (including chambers 72 and 74 seen in FIG. 10) that starts at the opening 70 and ends behind and adjacent to the closed front end 63; a plurality (e.g., three) of channels 68 formed at equiangular intervals (see FIG. 11); a plurality (e.g., three) of outer circumferential grooves 66 disposed along a common circle and extending between respective pairs of channels 68 (see FIG. 12); and an annular outer circumferential groove 65 (see FIGS. 9 and 10) disposed along a circle lying in a plane that is generally parallel to a plane of the common circle, the annular outer circumferential groove 65 being disposed between the annular lip 62 and the plurality of outer circumferential grooves 66.

The elastomeric body 60 further comprises a circular cylindrical surface 64 having relatively wide portions disposed between groove 65 and grooves 66 and relatively narrow portions disposed between groove 65 and recesses 68. The radius of circular cylindrical surface 64 (when the elastomeric body is not compressed) is slightly greater than an internal radius of the main chamber inside carpule 52, but less than the radius of lip 62, which also has a radius greater than the internal radius of the carpule main chamber.

Figure 10:
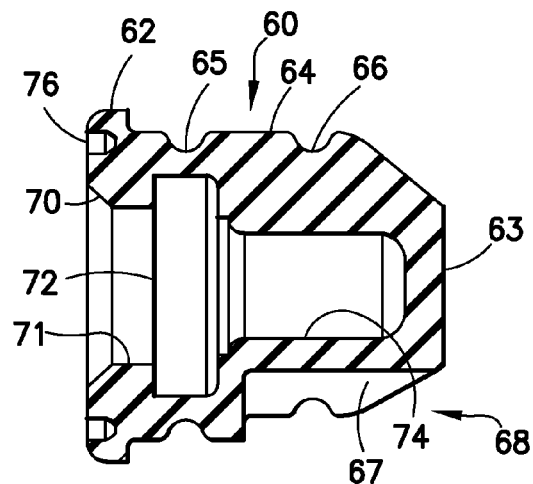
FIG. 10 is a drawing showing a cross-sectional view of the lyostopper/plunger of FIG. 9, the section being taken along a plane indicated by line 10-10 in FIG. 9.
Figure 11:
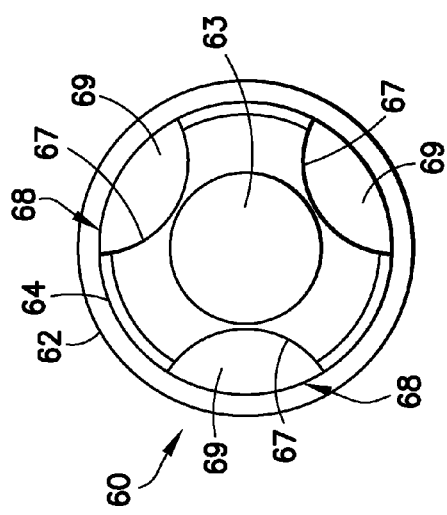
FIG. 11 is a drawing showing an end view of the lyostopper/plunger seen in FIGS. 8-10.
Figure 12:
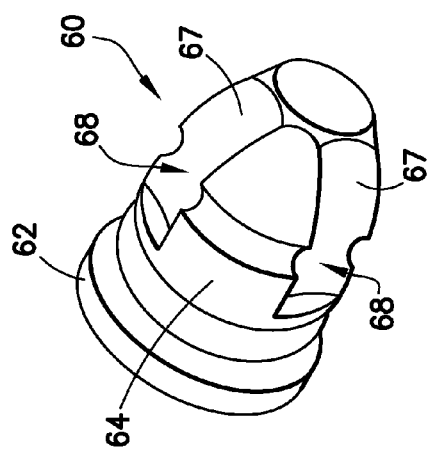
FIG. 12 is a drawing showing an isometric view of the lyostopper/plunger seen in FIGS. 8-11.

As should be apparent from FIGS. 10 and 11, each channel 68 is a recess bounded by a section of a circular cylindrical surface 67, the axis of such circular cylindrical surface being parallel to an axis of symmetry of the elastomeric body, and by a radial planar surface 69 (see FIG. 11) bounded by two circular arcs of different radii, the inner radius being equal to the radius of circular cylindrical surface 67 and the outer radius being equal to the radius of circular cylindrical surface 64.

Figure 9:
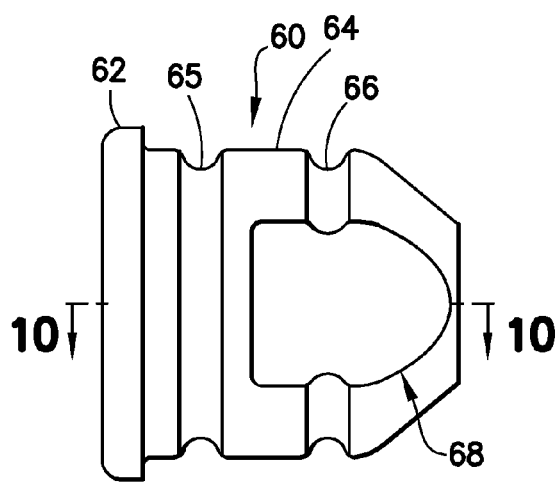
FIG. 9 is a drawing showing a side view of the lyostopper/plunger seen in FIG. 8.

The elastomeric body 60 further comprises an annular recess 76 and a central opening 70 formed in the rear end thereof. The annular recess 76 is concentric with and surrounds the chamfered circular central opening 70 and is bounded on its outer periphery by the annular lip 62. As seen in FIG. 9, the front end of the elastomeric body is tapered.

As seen in FIG. 10, the internal cavity comprises first (item 71), second (item 72) and third (item 74) circular cylindrical spaces having respective diameters and in fluid communication with each other. The second circular cylindrical space 72 is disposed between the first circular cylindrical space 71 and third circular cylindrical space 74. The diameter of the second circular cylindrical space 72 is greater than the diameter of the first circular cylindrical space 71 and greater than the diameter of the third circular cylindrical space 74. The internal cavity extends from a retracting portion of the elastomeric body (comprising lip 62) through a sealing portion (comprising surface 64) to a venting portion (comprising channel 68). Space 72 is sized and shaped to match a size and a shape of the head (see item 84 in FIG. 14) of a movable syringe element, as explained in detail below.

Bearing in mind the difficulty in describing portions of an integrally molded body which have no clear-cut boundaries, the functionality of the stopper/plunger shown in FIGS. 9-12 will now be described with reference to FIGS. 8 and 13-16.

Figure 13:
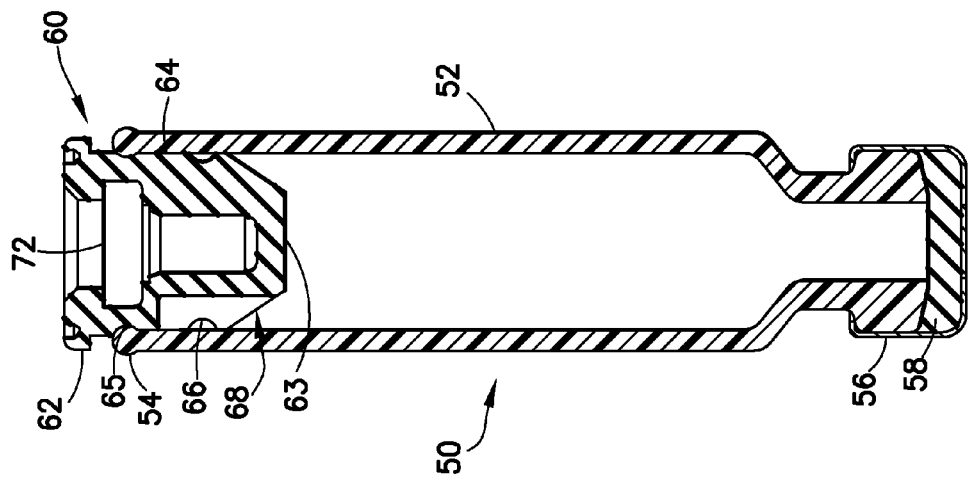
FIG. 13 is a drawing showing a cross-sectional view of the carpule of FIG. 8 with the lyostopper/plunger inserted deeper into the rear opening than is the case seen in FIG. 8, the rear opening of the carpule being sealed when the lyostopper/plunger is in this more fully inserted position.

As seen in FIGS. 8 and 13, assembly 50 comprises a glass carpule 52 having a bead 54 surrounding an opening at one end thereof and a stopper 60 partly inserted in carpule 52 at that one end. FIG. 8 shows stopper 60 partially inserted inside carpule 52 such that bead 54 of carpule 52 is seated in grooves 66, whereas FIG. 13 shows stopper 60 partially inserted further inside carpule 52 such that bead 54 of carpule 52 is seated in groove 65. Stopper 60 is placed in the position shown in FIG. 8 and then the carpule/stopper assembly 50 is placed inside a freeze dryer in order to freeze dry the solid matter (not shown) contained inside carpule 52. When the stopper is in the venting position shown in FIG. 8, the three recesses 68 (only one of which is visible in FIG. 8) allow vapors to be vented from the interior of carpule 52 during the freeze-drying operation, i.e., the interior of carpule 52 can be evacuated by the freeze dryer. When the freeze-drying process has been completed, the stopper 60 is pushed further into the carpule (by the freeze dryer) until it occupies the sealed position seen in FIG. 13. In the sealed position, stopper 60 maintains the vacuum inside carpule 52. The arrangement shown in FIG. 13 can also be used to seal a carpule containing liquid diluent rather than freeze-dried material.

In accordance with a further method of treating patients with injectable solutions, two carpule/stopper assemblies of the type depicted in FIG. 13 are installed in a housing of a syringe. These carpules are placed in an end-to-end relationship with a carpule containing solid matter in front of a carpule containing liquid diluent. During setup, a double-ended needle is attached to the front end of the syringe with one end of the needle puncturing the rubber membrane 58. Also a head on an outer hollow plunger rod of the syringe (previously described) is placed in a cavity 72 (see FIG. 10) of the stopper/plunger of the rear carpule. Preferably this cavity has the same shape and size as the head of the outer hollow plunger rod. A pointed inner hollow perforated rod of the syringe (previously described) is then extended to cause its tip to first pierce the stopper/plunger of the rear carpule. Then the pointed inner hollow perforated rod is further extended to cause its tip to pierce the sealed front opening of the rear carpule. Finally, the pointed inner hollow perforated rod is further extended to cause its tip to pierce the stopper/plunger of the front carpule. When the tip of the pointed inner hollow perforated rod is inside the front carpule (as seen in FIG. 5), the outer hollow plunger rod is extended, pushing the stopper/plunger of the rear carpule further into the rear carpule, thereby causing the liquid diluent in the rear carpule to be transferred into the front carpule via the pointed inner hollow perforated rod. As previously noted, this pre-mixing operation is carried out while the syringe is held upright in a vertical position, allowing air to vent out the needle as liquid is injected into the front carpule.

Inside the front carpule, the liquid diluent from the rear carpule is mixed with the solid matter in the front carpule, causing the latter to dissolve. With the mixing operation completed, both hollow rods are retracted from the carpules. In particular, when the inner hollow perforated rod is pulled out of the stopper/plunger of the front carpule, that stopper/plunger (made of elastomeric material) seals itself by closing the puncture hole. The rear (empty) carpule is then removed from the syringe housing.

In the next step in the procedure, the outer hollow plunger rod is extended until its head is inserted inside the cavity of the stopper/plunger of the front carpule. Then the physician inserts that needle into the patient and injects the mixture by extending the outer hollow plunger rod further so that its head pushes the stopper/plunger further into the first carpule. This causes the mixture solution in the front carpule to be injected into the patient.

In accordance with the embodiments disclosed herein, the stopper/plunger of the diluent-containing carpule performs the function of a plunger during transfer of the diluent into the carpule containing the freeze-dried solid matter, and then the stopper/plunger of the solution-containing carpule performs the function of a plunger during the injection of the solution into a patient. In the latter instance, the stopper/plunger also has structure to allow venting during the lyophilization process that produced the freeze-dried matter.

Figure 14:
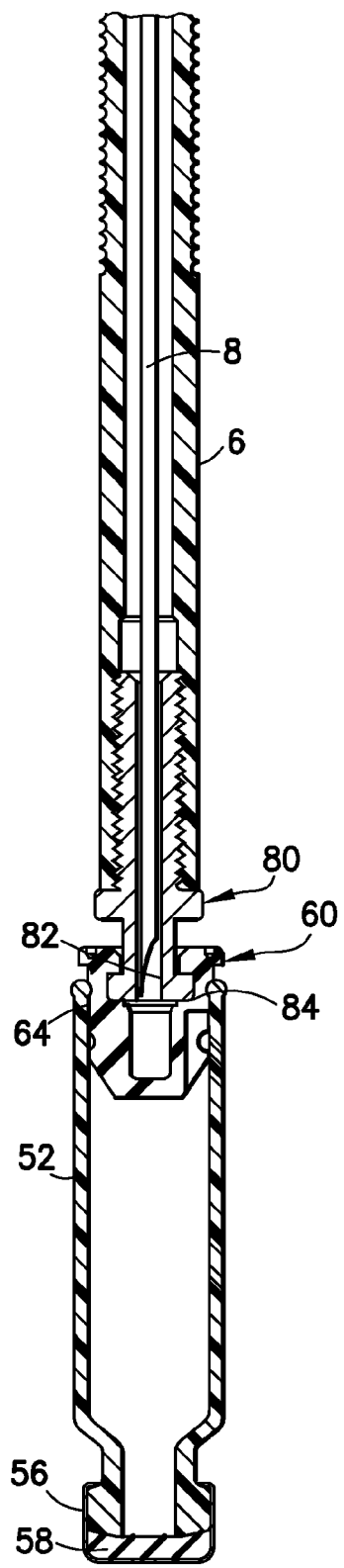
FIG. 14 is a drawing showing a cross-sectional view of portions of a syringe-carpule assembly in which a carpule has a lyostopper/plunger inserted in its rear opening in a sealed position, a flat head plunger rod screw mounted to the end of a outer hollow plunger rod of the syringe is inserted in a cavity in the lyostopper/plunger, and an inner hollow perforated rod of the syringe is in a retracted position.
Figure 15:
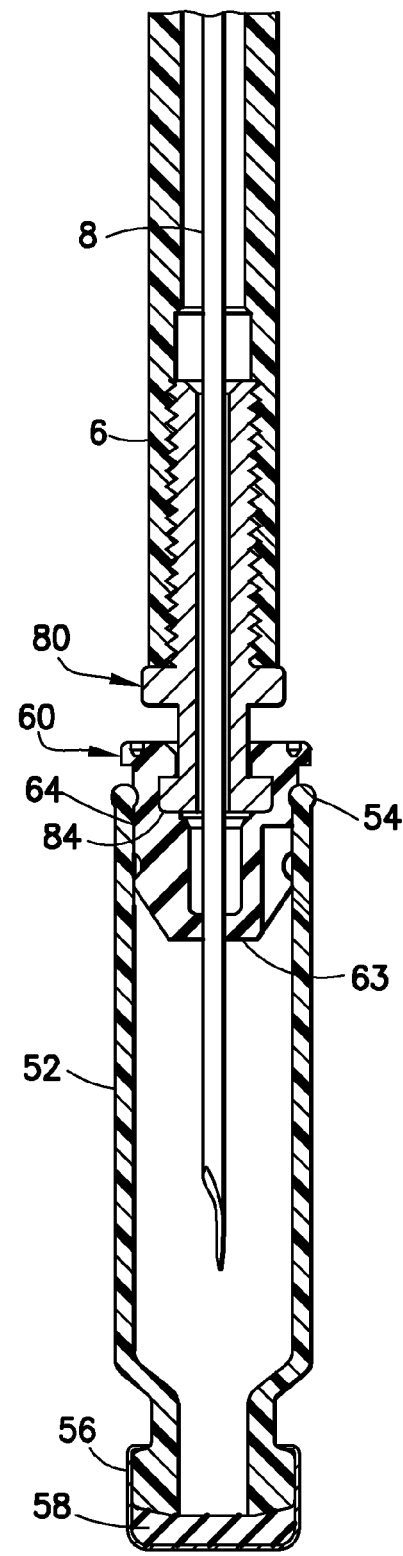
FIG. 15 is a drawing showing the same configuration as seen in FIG. 14, except that the inner hollow perforated rod of the syringe has been extended and pierced the lyostopper/plunger.

The structure of the syringe and its relationship to a carpule/stopper assembly at various stages of the process disclosed herein are partly shown in FIGS. 14-16. The syringe housing and the needle have been omitted in FIGS. 14-16 to facilitate viewing the structure housed in the housing. Also the perforations of the pointed inner hollow perforated rod 8 have been omitted from these drawings. (Such perforations have already been shown in FIGS. 4 and 5.)

FIG. 14 is a cross-sectional view of portions of a syringe-carpule assembly in which a carpule 52 has a lyostopper/plunger 60 inserted in its rear opening in a sealed position. A plunger rod screw 80 is mounted to the end of an outer hollow plunger rod 8 of the syringe. In the configuration shown in FIG. 14, the flat head 84 of plunger rod screw 80 is inserted in a cavity (cavity 72 shown in FIG. 13) in lyostopper/plunger 60. FIG. 14 also shows an inner hollow rod 6 of the syringe in a retracted position.

The flat head plunger rod screw 80 is shown in isolation in FIG. 17. In addition to flat head 84, the plunger rod screw 80 comprises a flange 86 and a threaded shaft 88. The threaded shaft screws into a threaded hole in outer hollow plunger rod 8 until flange 86 abuts the end of outer hollow plunger rod 8.

The carpule 52 depicted in FIG. 14 may contain either freeze-dried solid matter or liquid diluent. Although a lyostopper/plunger is not needed when the carpule contains liquid diluent (i.e., the venting channels of the lyostopper/plunger become superfluous), the use of a lyostopper/plunger for this purpose avoids the need to design a molded stopper/plunger having a different structure and requiring a different mold. Thus the coupling depicted in FIG. 14 accurately represents either a first configuration wherein flat head 84 is inserted in a lyostopper/plunger 60 of a carpule 52 containing liquid diluent (with the carpule containing freeze-dried matter not shown) or a second configuration wherein flat head 84 is inserted in a lyostopper/plunger 60 of a carpule 52 containing a solution of dissolved freeze-dried matter. The first configuration precedes the piercing of lyostopper/plunger 60 by the inner hollow perforated rod 6, which state is shown in FIG. 15. The second configuration precedes the injection of solution into the patient, which state is partly shown in FIG. 16 (the piercing of the rubber membrane 58 by the syringe needle is not shown).

FIGS. 14 and 15 will now be described assuming that carpule 52 represents the liquid diluent-containing rear carpule of a dual-carpule syringe. The other carpule, containing freeze-dried solid matter, is not shown in FIGS. 14 and 15, but would be in front of and aligned with carpule 52 were it shown. In FIG. 14, the lyostopper/plunger 60 is shown in the sealed position, whereby a circular cylindrical surface 64 of a sealing portion of the elastomeric body of lyostopper/plunger 60 bears against the internal surface of carpule 52, thereby sealing the rear opening of carpule 52. In FIG. 14, pointed inner hollow perforated rod 8 is shown in a retracted position inside a bore 82 of the flat head plunger rod screw 80. Likewise the outer hollow plunger rod 6 is shown in a retracted position, with head 84 of the flat head plunger rod screw 80 engaged in a cavity (cavity 72 in FIG. 13) of the lyostopper/plunger 60.

In contrast, FIG. 15 shows the pointed inner hollow rod 8 at an instant in time as it is being extended. In the extended position shown in FIG. 15, pointed inner hollow rod 8 has already pierced closed front end 63 of the elastomeric body that is lyostopper/plunger 60. As the pointed inner hollow rod 8 is extended further, it will next pierce the rubber membrane 58 and then the lyostopper/plunger of the carpule (not shown in FIG. 15) which is disposed in front of and aligned with carpule 52. FIG. 18 shows pointed inner hollow rod 8 in isolation and in its entirety.

Once the pointed inner hollow rod 8 has been fully extended, the physician must then extend the outer hollow plunger rod 6 in the forward direction. As outer hollow plunger rod 6 extends, the flat head 82 which is engaged with the lyostopper/plunger 60 carries the latter forward, pushing it further into the carpule 52, thereby pushing liquid diluent from the rear carpule into the solid matter-containing front carpule (not shown). FIG. 16 (described below) shows such a fully inserted position of a lyostopper/plunger, but in the context of pushing the latter through a carpule containing a solution of freeze-dried matter dissolved in liquid diluent.

FIGS. 14 and 16 will now be described assuming that carpule 52 represents the solution-containing front carpule of a dual-carpule syringe. The other carpule, containing liquid diluent, is assumed to have been removed after its contents were emptied into the front carpule 52 and is not shown in FIGS. 14 and 16 for purposes of this discussion. In FIG. 14, the lyostopper/plunger 60 is again shown in the sealed position, whereby a circular cylindrical surface 64 of a sealing portion of the elastomeric body of lyostopper/plunger 60 bears against the internal surface of carpule 52, thereby sealing the rear opening of carpule 52. In FIG. 14, pointed inner hollow perforated rod 8 is again shown in a retracted position inside a bore 82 of the flat head plunger rod screw 80. Likewise the outer hollow plunger rod 6 is shown in a retracted position, with head 84 of the flat head plunger rod screw 80 engaged in a cavity (cavity 72 in FIG. 13) of the lyostopper/plunger 60.

In contrast, FIG. 16 shows the outer hollow plunger rod 6 at an instant in time as it is being extended. As outer hollow plunger rod 6 extends, the flat head 82 which is engaged with the lyostopper/plunger 60 carries the latter forward, pushing it further into the carpule 52, thereby pushing solution from the front (and only remaining) carpule into a needle attached to the front end of the syringe housing (see FIG. 7), thereby injecting the solution into the patient.

Referring back to FIG. 13, the lyostopper/plunger 60 comprises an annular lip 62 having an outer diameter that is greater than an inner diameter of an interior chamber of carpule 52. The elastomeric body that is lyostopper/plunger 60 has an axis of symmetry and further comprises an annular recess (item 76 in FIG. 10) having the axis of symmetry as its center point. This annular recess is bounded on its outer periphery by lip 62. Although not depicted in detail in FIG. 16, lip 62 flexes radially inwardly as the lyostopper/plunger 60 is pushed into the interior chamber of carpule 52. Thus the resistance of lip 62 to entry into carpule 52 as the outer hollow plunger rod 6 is extended is easily overcome and the outer circumferential surface of lip 62 provides an additional sealing surface when the lyostopper//plunger 60 is in a fully inserted position such as that shown in FIG. 16.

The system disclosed herein enables the delivery of drugs that come in two forms (i.e. lyophilized matter or powder and liquid solvent) that need to be premixed in an easy, single use, such as when injecting botulinum toxin. Mixing of the two ingredients in a disposable vial sized to hold a single dosage avoids the waste that accompanies mixing larger volumes of ingredients in a bottle to produce a batch of doses that must be used within a fixed time frame. The present invention facilitates effective and cost efficient mixing of a single dosage of ingredients, thereby reducing the cost of drug application.

The lyostopper/plunger disclosed herein allows mixing of a lyophilized drug in a single-dose carpule, with immediate injection of the solution. The mixture does not have to be drawn up in a second syringe. This avoids any cross contamination in the process of drawing up a secondary syringe or in multiple uses of a multi-dose vial.

Another advantage is that the invention avoids human error in mixing the liquid and powder in the correct ratio. A further advantage lies in the fact the invention minimizes spill-off and residual medication in the multiple syringes that are used to draw up the medications in a multi-dose vial (each drop of medicine can be very expensive).

Lastly, the apparatus disclosed herein avoids the cost of using ancillary equipment (i.e., syringes) by eliminating the process of drawing up a secondary syringe. This is environmentally friendly because there will be less usage of disposable syringes.

While the invention has been described with reference to various embodiments, it will be understood by those skilled in the art that various changes may be made and equivalents may be substituted for elements thereof without departing from the scope of the invention. In addition, many modifications may be made to adapt a particular situation to the teachings of the invention without departing from the essential scope thereof. Therefore it is intended that the invention not be limited to the particular embodiment disclosed as the best mode contemplated for carrying out this invention.

As used in the claims, the term "channel" should be construed broadly to include both tubular and trough-shaped passages for fluids.

The method claims should not be construed to require that the recited steps be performed in alphabetical order or in the order in which they are recited.

The invention claimed is:

1. An assembly comprising a carpule comprising a bead surrounding an opening at one end thereof and a stopper at least partly inserted in said carpule at said one end, said stopper being a body of elastomeric material comprising a venting portion, a sealing portion and a retracting portion, said venting portion comprising at least one venting channel and at least one outer circumferential groove for receiving a portion of said carpule bead when said elastomeric body is partly inserted in said carpule in a venting position, said sealing portion comprising an annular outer circumferential groove for receiving said carpule bead when said elastomeric body is inserted further but not fully in said carpule in a sealing position, and said retracting portion comprising a lip that is disposed outside said carpule when said elastomeric body is partly inserted in said carpule and that flexes radially inward when said elastomeric body is fully inserted in said carpule, said sealing portion being disposed between said venting portion and said retracting portion.

2. The assembly as recited in claim 1, wherein said elastomeric body further comprises an internal cavity that extends from said retracting portion through said sealing portion to said venting portion, said internal cavity comprising a section sized and shaped to match a size and a shape of a movable syringe element.

3. The assembly as recited in claim 2, wherein said elastomeric body further comprises a pierceable central tip disposed at a forward end of said internal cavity.

4. The assembly as recited in claim 1, wherein said lip has an outer diameter greater than an inner diameter of an interior chamber of said carpule.

5. The assembly as recited in claim 1, wherein said elastomeric body has an axis and further comprises an annular recess having said axis as its center point, said annular recess being bounded on its outer periphery by said lip.

6. The assembly as recited in claim 1, wherein said at least one venting channel allows fluid communication between an interior and an exterior of said carpule when said elastomeric body is partly inserted in said carpule in said venting position.

* * * * *